United States Patent [19]
Yang

[11] Patent Number: 5,457,596
[45] Date of Patent: Oct. 10, 1995

[54] STATIC ELECTRICITY PROTECTION WRIST STRAP

[76] Inventor: Hsin-Ming Yang, 4F, No. 1, Lane 560, Chung Cheng Road, Hsin Tien City, Taipei Hsien, Taiwan

[21] Appl. No.: 82,203

[22] Filed: Jun. 24, 1993

[51] Int. Cl.⁶ .................................................. H05F 03/02
[52] U.S. Cl. ............................................ 361/220; 361/212
[58] Field of Search ................................. 361/212, 220, 361/221, 222, 223, 224; 324/509, 72.5, 457, 686, 690; 340/649, 573

[56] References Cited

U.S. PATENT DOCUMENTS

| | | | |
|---|---|---|---|
| 4,558,309 | 12/1985 | Antonevich | 340/649 |
| 4,638,399 | 1/1987 | Maroney et al. | 361/220 |
| 4,720,764 | 1/1988 | Lucas | 361/212 |
| 4,745,519 | 5/1988 | Breidegam | 361/220 |
| 4,813,459 | 3/1989 | Breidegam | 139/421 |
| 4,845,585 | 7/1989 | Weiss | 361/220 |
| 4,862,315 | 8/1989 | Cubbison, Jr. | 361/212 |
| 5,164,674 | 11/1992 | Bakhoum | 361/212 X |
| 5,179,497 | 1/1993 | Bakhoum | 361/212 |

*Primary Examiner*—A. D. Pellinen
*Assistant Examiner*—Fritz M. Fleming

[57] ABSTRACT

A static electricity protection wrist strap comprises a casing inside which a conductive plate is mounted. The conductive plate has serrated side extensions for engaging a strap extending from one side of the casing, around the wrist of a user and back to connect to the other side of the casing. A grounding wire in electrical connection with the conductive plate provides the static electricity protection wrist strap a grounding connection. A static electricity detection device comprises a detection plate which constitutes a capacitor with the skin of the wrist wearing the wrist strap and a processing unit for detecting the variation of the capacitor. The processing unit comprises a beeper which will be actuated to send out a warning signal when an increase of the static electricity collected on the wrist skin is detected.

5 Claims, 5 Drawing Sheets

STATIC ELECTRICITY PROTECTION WRIST STRAP

FIELD OF THE INVENTION

The present invention relates generally to a static electricity dissipation wrist strap and in particular to such a wrist strap with a static electricity detector.

BACKGROUND OF THE INVENTION

In the electronic industry, static electricity protection is one of the major concerns in the manufacturing processes. For example, the complementary-symmetry metal oxide semiconductor (CMOS) which is very common to the computer and communication industries is very sensitive to static electricity during manufacturing or assembling. For the electronic element manufacturers, protection against the static electricity is very important.

Conventionally, an electrically conductive bracelet, commonly called wrist strap, is wron on the wrist of a manufacturing operator of an electronic element manufacturing factory. A conductive wire is connected between the wrist strap and ground for transferring the static electric charges collected on the wrist strap to ground so as to protect the electronic elements manufactured or manipulated by the operator from being damaged by the static electricity.

One of the disadvantages of the conventional wrist strap is that the operator has to watch the grounding wire to prevent the grounding wire from being accidently out of contact with ground and thus resulting in a static electricity damage to the electronic elements. Further, if the grounding wire is damaged and thus losses the conductivity thereof, inspection has to be done with instruments sometimes. Such a situation may be overlooked and thus resulting in damage.

It is therefore desirable to provide a static electricity protection wrist strap which incorporates static electicty detection device to overcome the above-mentioned problems of the prior art wrist strap.

SUMMARY OF THE INVENTION

It is therefore the principal objective of the present invention to provide a static electricity protection wrist strap which compirses an electricity detection device in the line connecting ground so as to provide an indication of the damage of the grounding wire to prevent an unexpected static electricity accident.

To achieve the above objective, there is provided a static electricity protection wrist strap comprising a casing inside which a conductive plate is mounted. The conductive plate has serrated side extensions for engaging a strap extending from one side of the casing, around the wrist of a user and back to connect to the other side of the casing. A grounding wire in electrical connection with the conductive plate provides the static electricity protection wrist strap a grounding connection. A static electricity detection device comprises a detection plate which constitutes a capacitor with the skin of the wrist wearing the wrist strap and a processing unit for detecting the variation of the capacitor. The processing unit comprises a beeper which will be actuated to send out a warning signal when an increase of the static electricity collected on the wrist skin is detected.

BRIEF DESCRIPTION OF THE DRAWINGS

The present invention will be better understood from the following description of a preferred embodiment of the present invention, with reference to the attached drawings, wherein.

DETAILED DESCRIPTION OF THE PREFERRED EMBODIMENT

Figure 1:
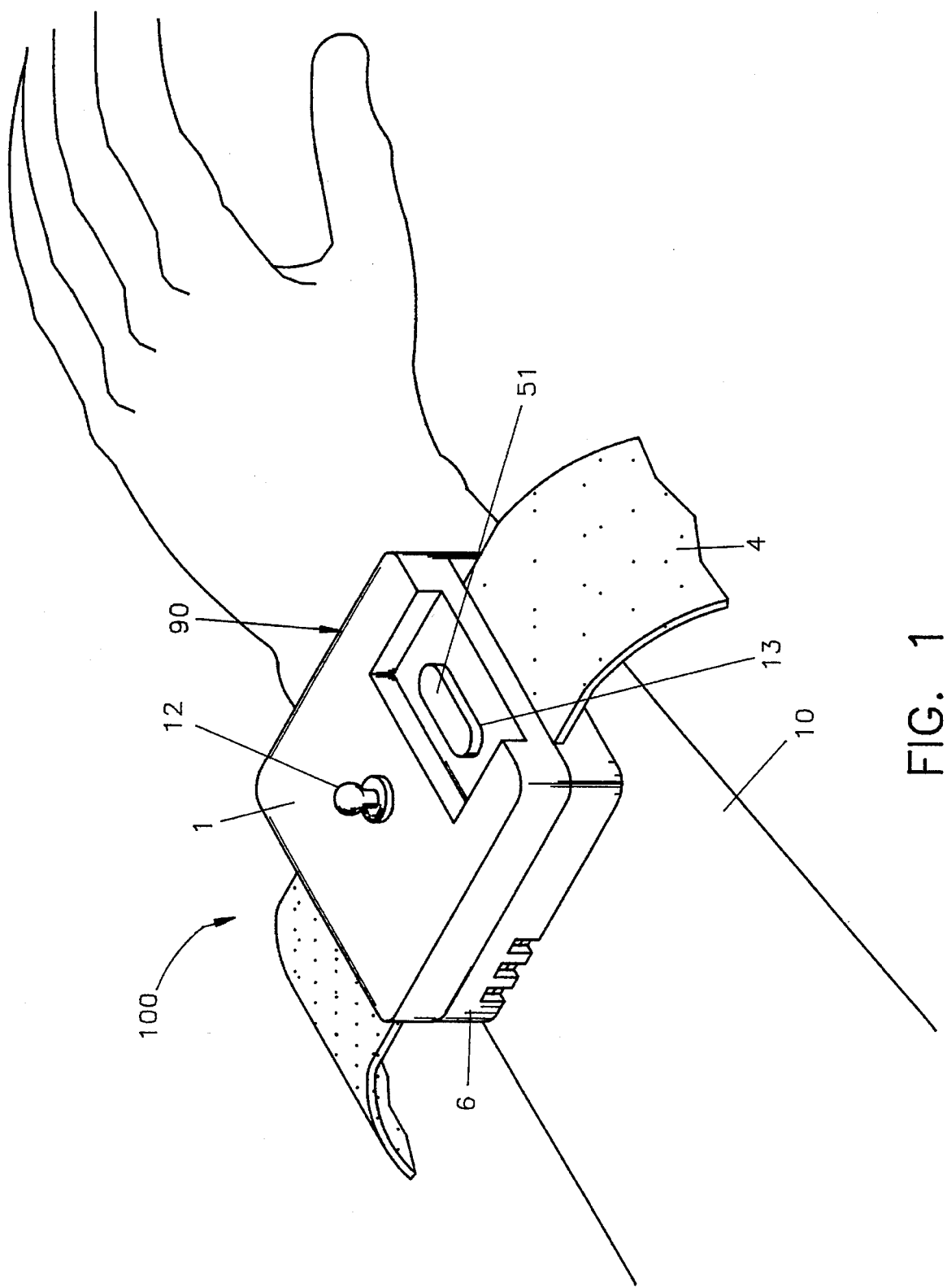
FIG. 1 a perspective view showing a wrist strap constructed in accordance with the present invnetion with the grounding wire removed.
Figure 2:
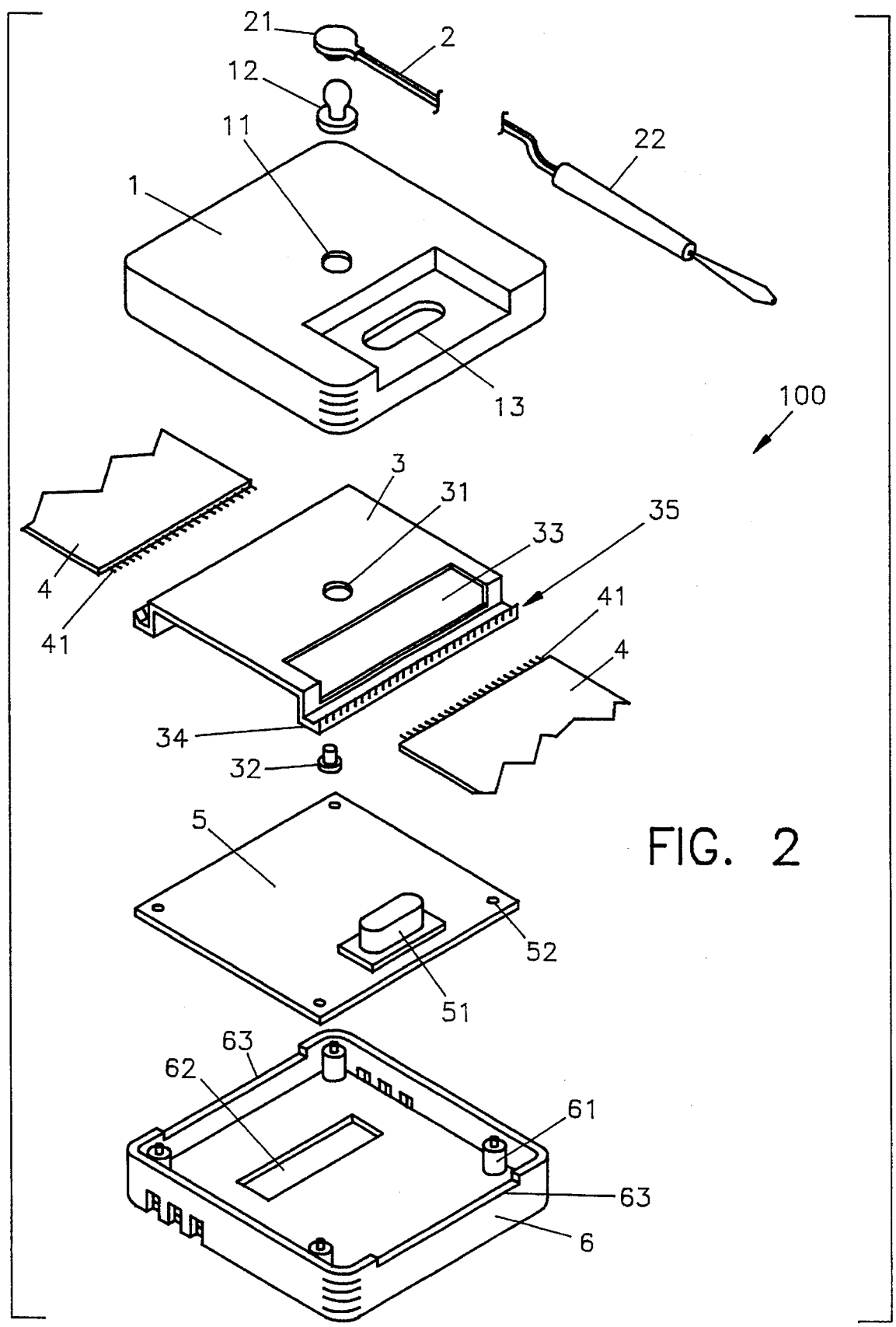
FIG. 2 is an exploded perspective view showing the wrist strap of the present invention.

With reference to the drawings and in particular to FIGS. 1 and 2, wherein a static electricity wrist strap constructed in accordance with the present invention, generally designated by the reference numeral 100, is shown, the wrist strap 100 comprises a casing 90 constituted by a cover member 1 matingly secured to a base member 6 to define therein an interior space for receiving the static electricity detection device comprising a circuit board 5 which will be further described hereinafter.

The cover member 1 is made of an electrical insulation material, having formed thereon a through hole 11 into which a conductive plug 12 is inserted and secured therein. A conductuve grounding wire 2 has a connector 21 mounted to one end therof engageable by the plug 12. The grounding wire 2 further has a grounding contact 22 formed on the opposite end thereof for electrical connection to ground.

The cover member 1 also has a through slot 13 to allow a switch button 51 which is disposed on the circuit board 5 to extend therethrough to be operated by a user.

Figure 3:
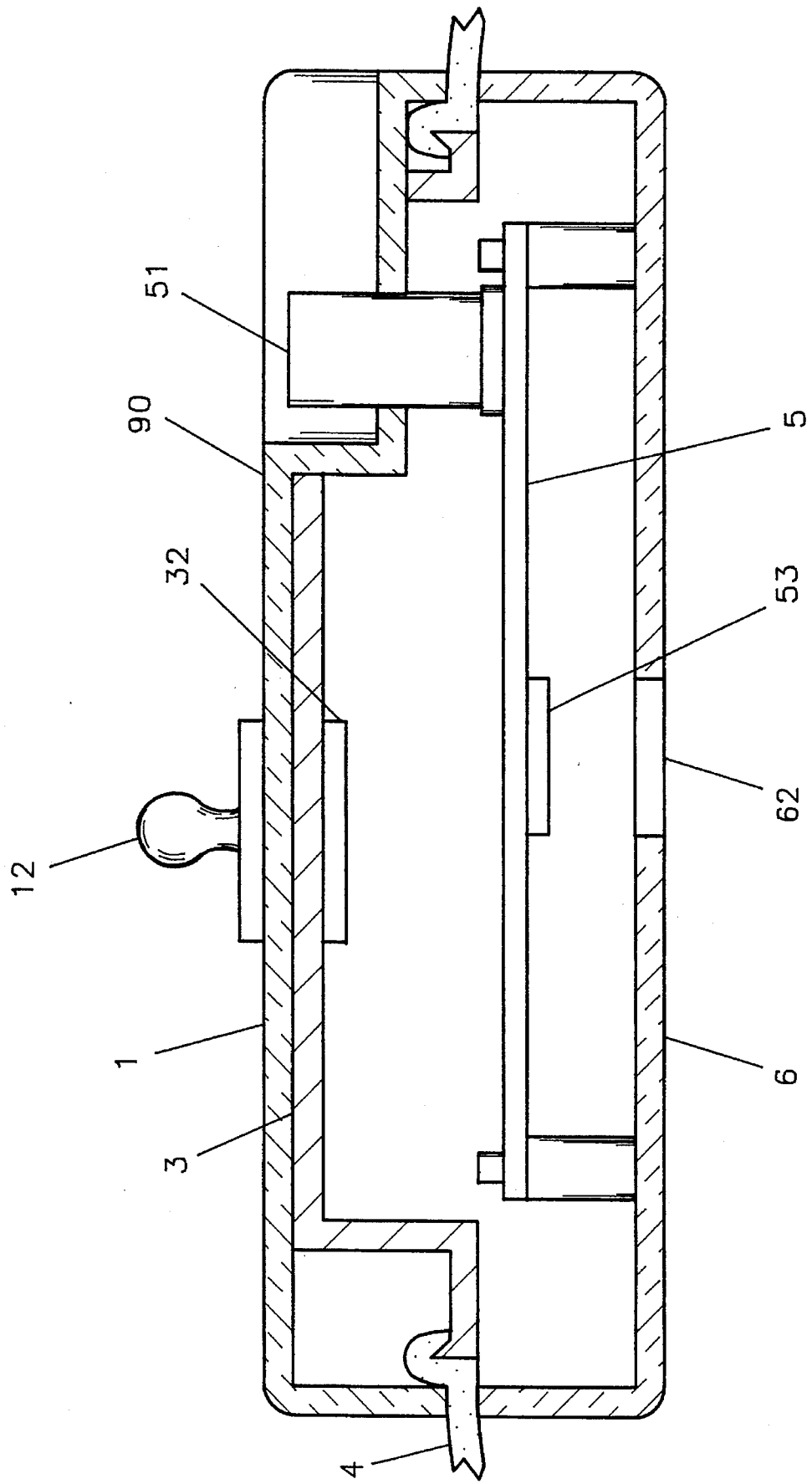
FIG. 3 is a cross-sectional view showing the wrist strap of the present invention with the grounding wire removed.

Within the interior space defined by the casing 90, an electical conductive plate 3 is disposed to be substantially received within the cover 1 and above the circuit board 5. The plate 3 has formed theron a hole 31 corresponding to the through hole 11 to allow a fastener, such as a rivet 32, extending therethrough to secure the plug 12 on the casing 90 and fix the plate 3 to the underside of the cover 1, as illustrated in FIG. 3.

The plate 3 has also a through slot 33 to allow the switch button 51 to extend therethrough and through the through slot 13 of the cover member 1 so as to project out of the casing 90 to be accessable by the user.

The plate 3 has two opposite side extensions 34 with sharp serrations 35 formed thereon for penenrtating and thus holding thereon a strap member 4 which is worn around a wrist of the user. The penetration of the sharp serrations 35 into the strap member 4 allows the plate 3 to establish an electrical connection with conductive filaments 41 disposed within the strap member 4 so that the static electricity collected on the skin of the user 10 can be conducted to ground through the conductive filaments 41, the conductive plate 3, the plug 12 and the grounding wire 2.

The securing of the strap member 4 to the casing 90 may be enhanced by the tight engagement between the cover member 1 and the base member 6.

As illustrated in FIGS. 2 and 3, the circuit board 5 is disposed between the conductive 3 and the base member 6 of the casing 90. Preferably, the circuit board 5 has a number of seucring holes 52 into which posts 61 extending from the base member 6 are respectively tightly fit or, alternately, fasteners (not shown) are received for securing the circuit board 5 to the base member 6.

The casing 90 comprises side openings 63 to allow the strap member 4 to extend therethrough for winding around the wrist of the user.

The base member 6 and the posts 61 thereof are made of an elecrical insulation material to ensure electrical insulation of the circuit board 5.

Figure 4:
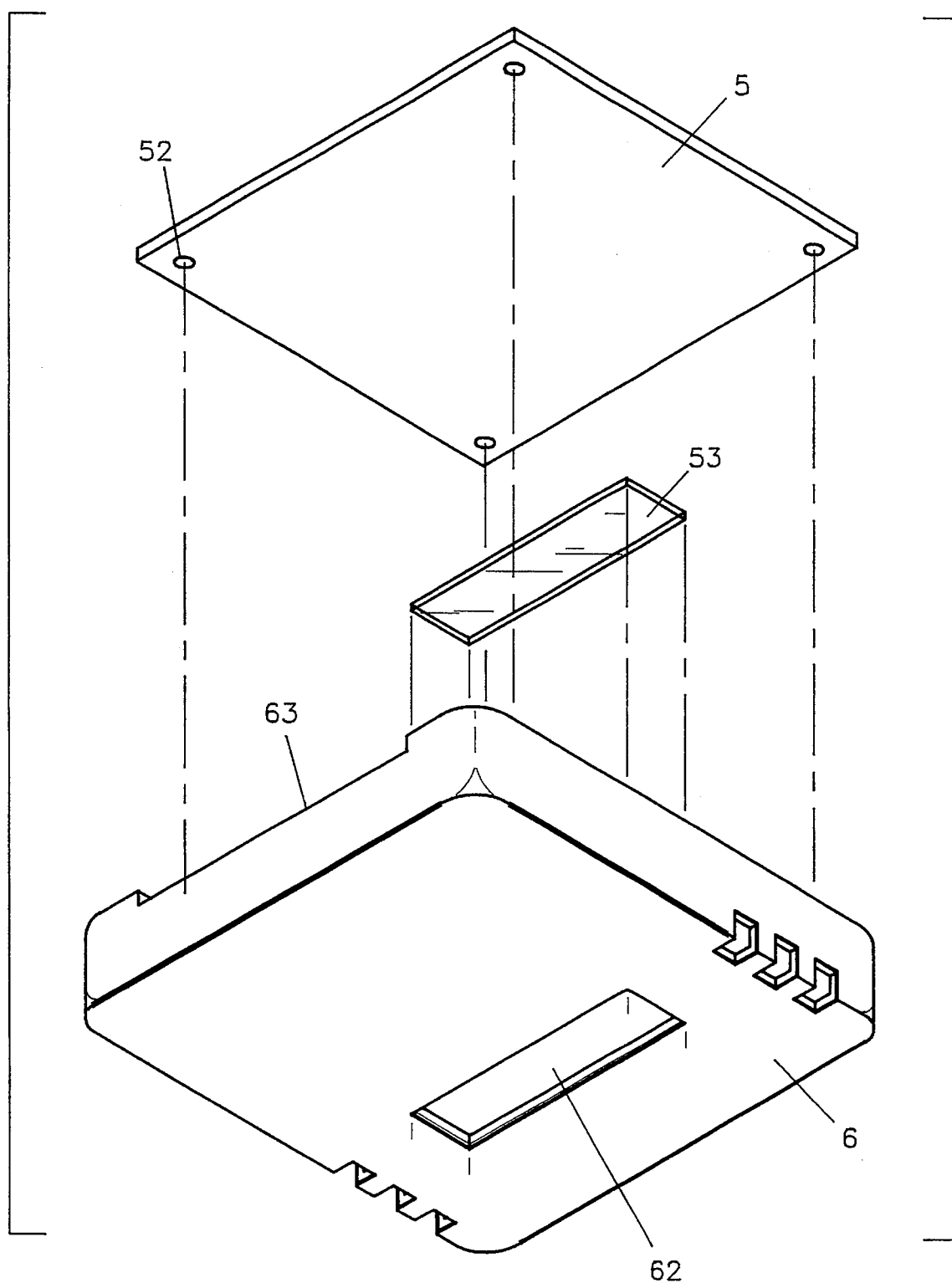
FIG. 4 is a perspective view showing the casing of the static electricity detection device adopted in the wrist strap of the present invention.

Further, the base member 6 has a bottom opening 62 which when the wrist strap 100 is worn faces the wrist skin of the user 10. This bottom opening 62 is also shown in FIG. 4. As shown, a detection plate 53 is fixed on the under side of the circuit board 5 and in electrical connection therewith. The detection plate 53 is disposed at such a location to be substantially opposite to the bottom opening 62 of the base member 6 so as to form a capacitor structure with the wrist skin of the user.

Figure 5:
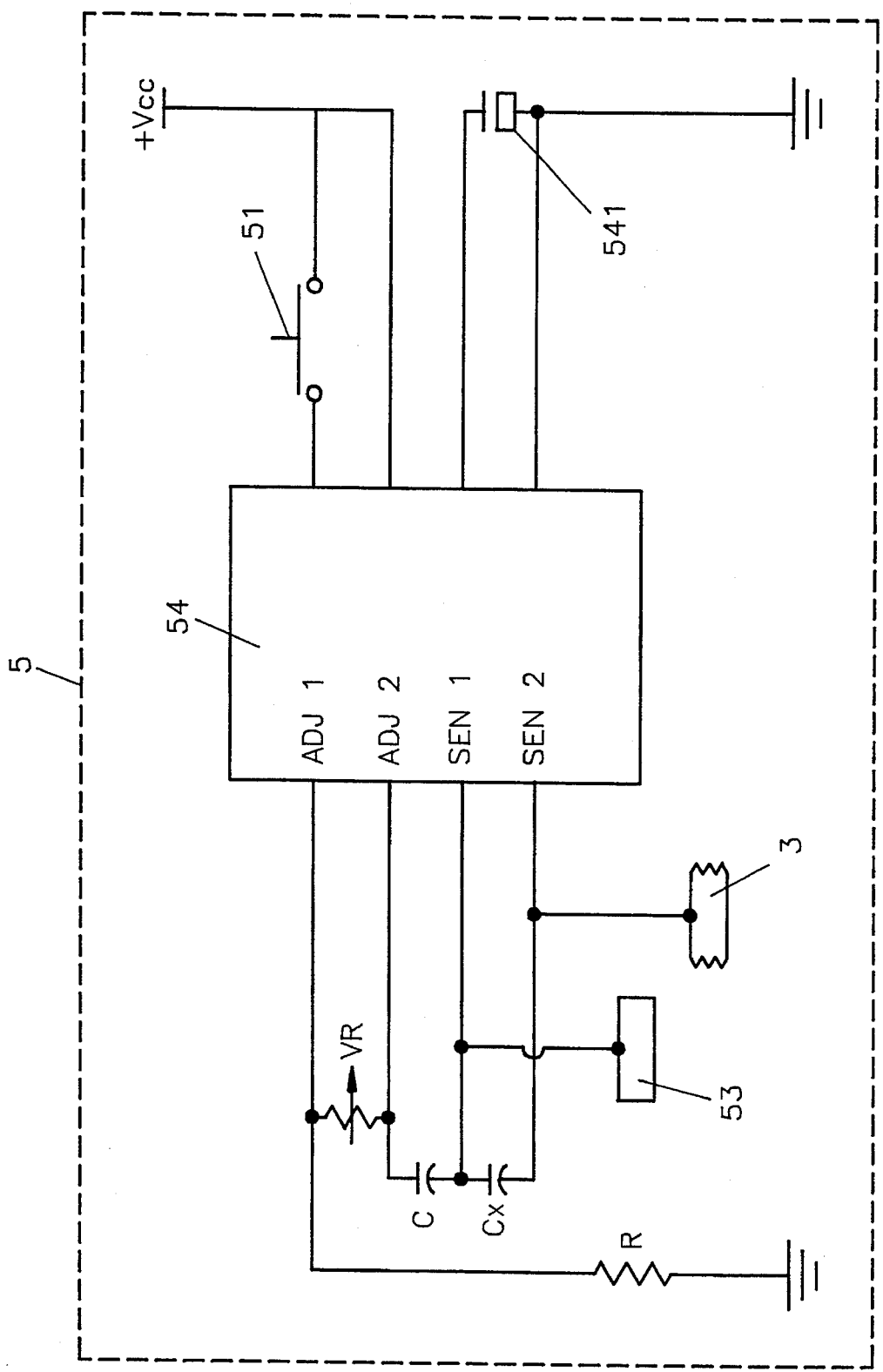
FIG. 5 is a circuit diagram of an embodiment of the static electricity device adopted in the wrist strap of the present invention.

An embodiment of the circuit of the static electricity detection device is illustrated in FIG. 5. The detection device comprises an integrated circuit (IC) chip 54 which serves as a processing unit mounted on the circuit board 5. Two adjusting pins ADJ1 and ADJ2 of the IC chip 54 are connected together by a variable resistor VR and a resistor R is connected between the pin ADJ1 and ground to provide sensitivity adjustment to the IC chip 54. The IC chip 54 comprises a first sensing pin SEN1 connected to detection plate 53 and a second sensing pin SEN2 connected to the conductive plate 3 and the strap member 4 to form a capacitor Cx. The pins SEN1 and ADJ2 have a reference capacitor C connected therebetween. Once a variation or increase of the electric charges collected on the detected capacitor Cx occurs, a signal is detected by the ciruit 0 and the IC chip 54 actuates a warning device 541, such as a beeper, to indicate the potential danger induced by the great charges collected on the detected capacitor Cx.

A power source Vcc is connected to the IC chip 54 via the switch button 51 so that the user may actuate the circuit by the switch 51.

The detection device allows the user to be informed of the excess charge collected on the plate 53 which indicates a potential damage so that the user may take actions to prevent the static electricity damage.

It is apparent that although the invention has been described in connection with the preferred embodiment, it is contemplated that those skilled in the art may make changes to certain features of the preferred embodiment without altering the basic concept of the invention and without departing from the spirit and scope of the invention as defined in the appended claims.

What is claimed is:

1. A static electricity protection wrist strap comprising:
   a casing having an electrical insulation cover member tightly engaging an elecrical insulation base member to define therein an interior space;
   a conductive plate disposed inside said interior space to be substantially fit under said cover member, said conductive plate comprising two opposite side extensions each having sharp serrations formed thereon;
   a strap member having conductive filaments contained therein extending from one of the serrated side extensions of said conductive plate, through a side opening formed on said casing to outside said casing to surround a wrist of a user and returning through a second side opening of said casing to connect to the other one of the serrated side extensions, said serrations penetrating said strap member to electrically contact the conductive filaments inside said strap member;
   a conductive plug extending through a hole formed on said cover member and a corresponding hole formed on said conductive plate to project out of said casing and secured thereto by a fastener;
   a conductive wire connected between said conductive plug and ground;
   a static electricity detection device comprising a circuit board disposed inside said interior space and below said conductive plate to oppose said base member, said circuit board being in electrical connection with said conductive plate and having a detection plate mounted on a under side thereof to face a corresponding bottom opening formed on said base member so as to allow the detection plate and skin of the wrist to form a capacitor structure of which the charge capacity is to be detected, said circuit board comprising an actuation switch for actuating the static electricity detection device; and
   a warning device which sends out a warning signal once the detected charge capacity exceeding a pre-set level.

2. A static electricity protection wrist strap as claimed in claim 1, wherein said circuit board further comprises an integrated ciruciit processing unit having a first adjusting pin and a second adjusting pin with a variable resistor connected therebetween and a second resistor connected between the first adjusting pin and ground to provide an adjustment of sensitivity of the detection device, said processing unit further comprising a first sensing pin in connection with the detection plate and a second sensing pin in connection with the wrist skin via the conductive plate and the strap member so as to form the capacitor to be detected, a second capacitor being connected between the first sensing pin and the second adjusting pin of the processing unit.

3. A static electricity protection wrist strap as claimed in claim 2, wherein said actuation switch comprises a button mounted on the circuit board, said switch connecting a power source to the processing unit so that by closing the switch, the power is allowed to be applied to processing unit to operate the processing unit.

4. A static electricity protection wrist strap as claimed in claim 3, wherein said button projects out of the casing through slots formed on the casing and the conductive plate.

5. A static electricity protection wrist strap as claimed in claim 1, wherein said warning device comprises a beeper.

* * * * *